(12) United States Patent
Yokoi et al.

(10) Patent No.: US 7,573,025 B2
(45) Date of Patent: Aug. 11, 2009

(54) ENERGY CALIBRATION METHOD AND RADIATION DETECTING AND RADIOLOGICAL IMAGING APPARATUS

(75) Inventors: Kazuma Yokoi, Hitachi (JP); Kensuke Amemiya, Hitachinaka (JP); Keiji Kobashi, Mito (JP); Tomoyuki Seino, Hitachi (JP); Takafumi Ishitsu, Hitachi (JP); Isao Takahashi, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/676,702

(22) Filed: Feb. 20, 2007

(65) Prior Publication Data

US 2007/0228267 A1    Oct. 4, 2007

(30) Foreign Application Priority Data

Mar. 31, 2006   (JP) ............................. 2006-096374

(51) Int. Cl.
   *G01D 18/00*   (2006.01)
(52) U.S. Cl. .................................... 250/252.1
(58) Field of Classification Search .............. 250/252.1, 250/370.01–370.15
   See application file for complete search history.

(56) References Cited

U.S. PATENT DOCUMENTS

| | | | | |
|---|---|---|---|---|
| 4,893,018 A | * | 1/1990 | Saitou | 250/370.1 |
| 5,489,775 A | * | 2/1996 | Viera | 250/252.1 |
| 6,329,651 B1 | * | 12/2001 | Mestais et al. | 250/252.1 |

FOREIGN PATENT DOCUMENTS

JP    3566398    4/2004

* cited by examiner

*Primary Examiner*—David P Porta
*Assistant Examiner*—Kiho Kim
(74) *Attorney, Agent, or Firm*—Mattingly & Malur, PC

(57) ABSTRACT

The energy calibration method detects irradiation of radiation with predetermined energy from a calibration radiation source using a plurality of radiation detectors having a peak value distribution whose mode and mean value are different and performs calibration so that mean values become identical within the peak value distributions of the respective radiation detectors obtained through irradiation of radiation with predetermined energy from the calibration radiation source.

14 Claims, 3 Drawing Sheets

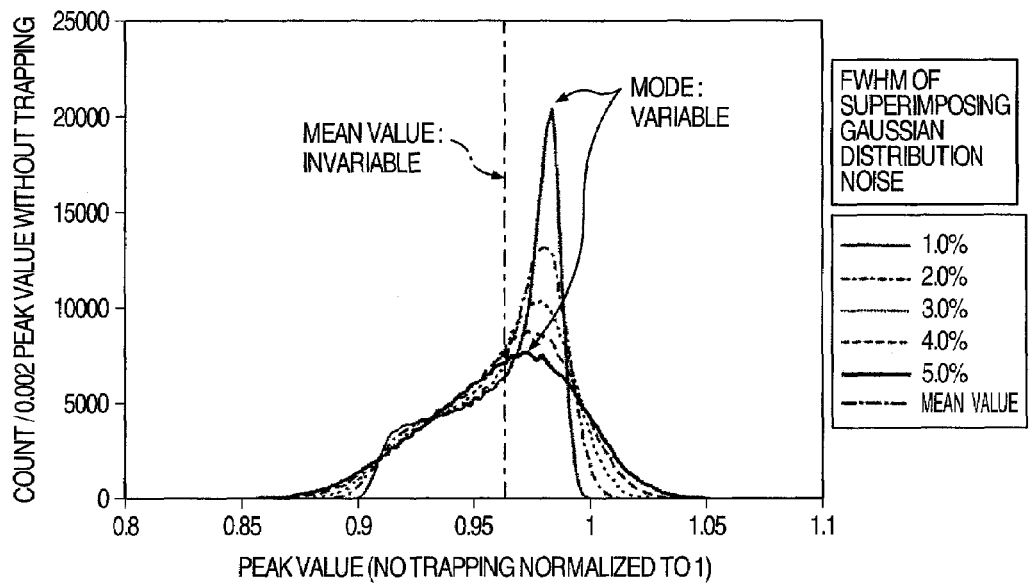
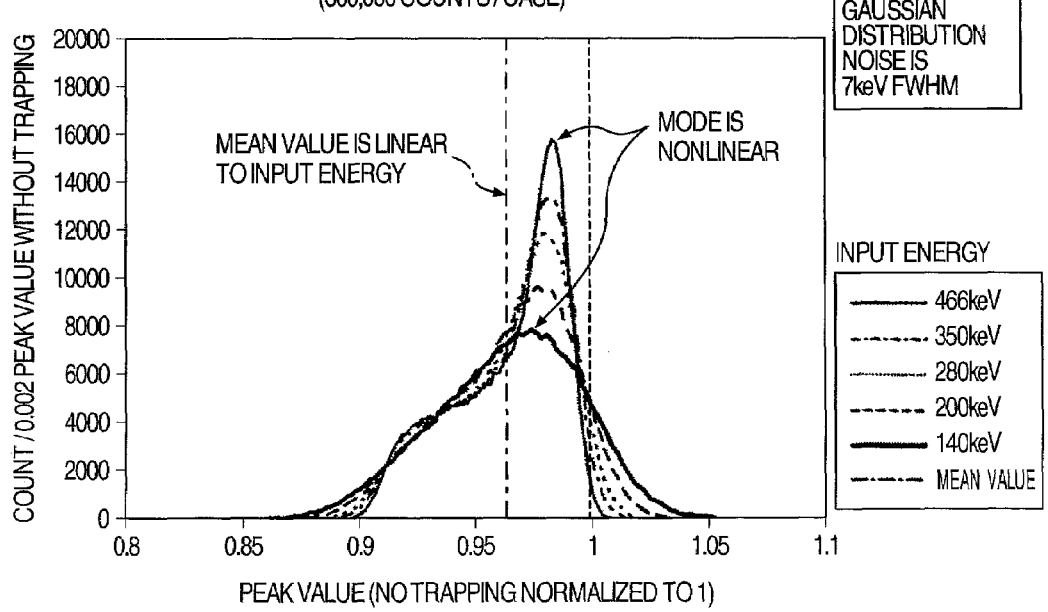

FIG.5
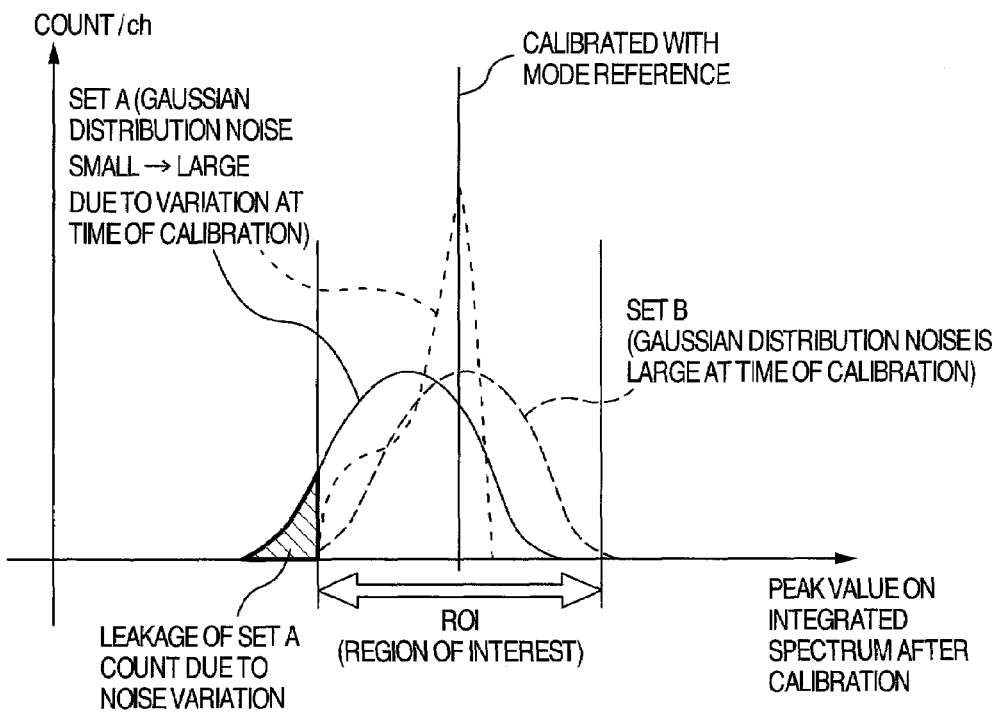
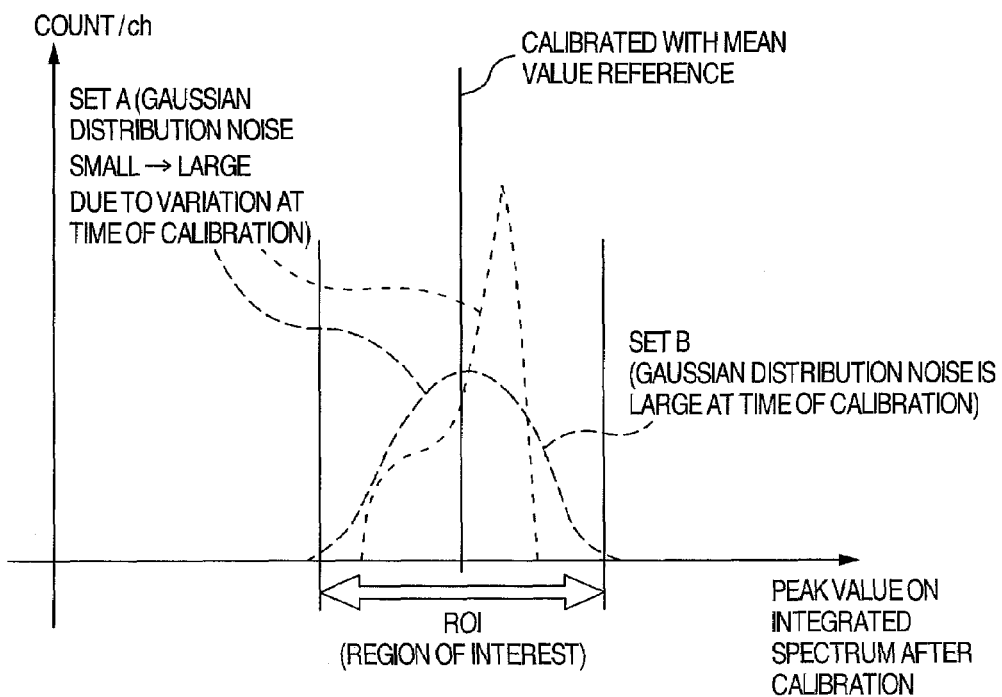

ENERGY CALIBRATION METHOD AND RADIATION DETECTING AND RADIOLOGICAL IMAGING APPARATUS

BACKGROUND OF THE INVENTION

The present invention relates to an energy calibration method for radiation detectors and a radiological imaging apparatus subjected to energy calibration.

Examples of conventional calibration methods for calibrating a radiation detector include one described in Japanese Patent No. 3566398. This method calibrates energy in such a way that a peak value of an energy spectrum obtained from an output signal of each pixel is equal over a whole image area [0006]. Even when there is scattered radiation, this method determines a peak value of the energy spectrum so that the energy peak falls within a predetermined channel (an index value set for each energy value independently at each pixel) and calibrates an energy calibration coefficient of each pixel using an overall calibration coefficient Z derived from this peak value [0038].

SUMMARY OF THE INVENTION

The following problems have been discovered; that a mode of a peak value distribution also fluctuates for the same incident energy due to a variation in the amount of other noise (electronic noise or the like) because of asymmetry of trapping loss noise and that a measured peak value is made nonlinear due to dependency of trapping loss noise on the peak value even when the amount of other noise is constant. It is an object of the present invention to solve the above described two problems and provide a stable and linear energy reference against variations in the amount of electronic noise or the like.

The present invention provides an energy calibration method detecting irradiation of radiation with predetermined energy from a calibration radiation source using a plurality of radiation detectors having a peak value distribution whose mode and mean value are different and performing calibration so that mean values become identical within peak value distributions of the respective radiation detectors obtained through irradiation of radiation with predetermined energy from the calibration radiation source.

The present invention can obtain high energy calibration accuracy regardless of noise and magnitude of incident energy.

Other objects, features and advantages of the invention will become apparent from the following description of the embodiments of the invention taken in conjunction with the accompanying drawings.

BRIEF DESCRIPTION OF THE DRAWINGS

FIG. 3 shows a peak value distribution variation (transfer of mode) according to an amount of superimposing noise of the semiconductor detection element;

FIG. 4 shows nonlinearity of a mode position in an energy spectrum of the semiconductor detection element; and FIG. 5 shows a relationship between a noise variation and an ROI.

DESCRIPTION OF THE INVENTION

An example of a semiconductor detection apparatus and a radiological imaging apparatus using the semiconductor detection apparatus will be explained in detail with reference to the attached drawings as appropriate.

Figure 1:
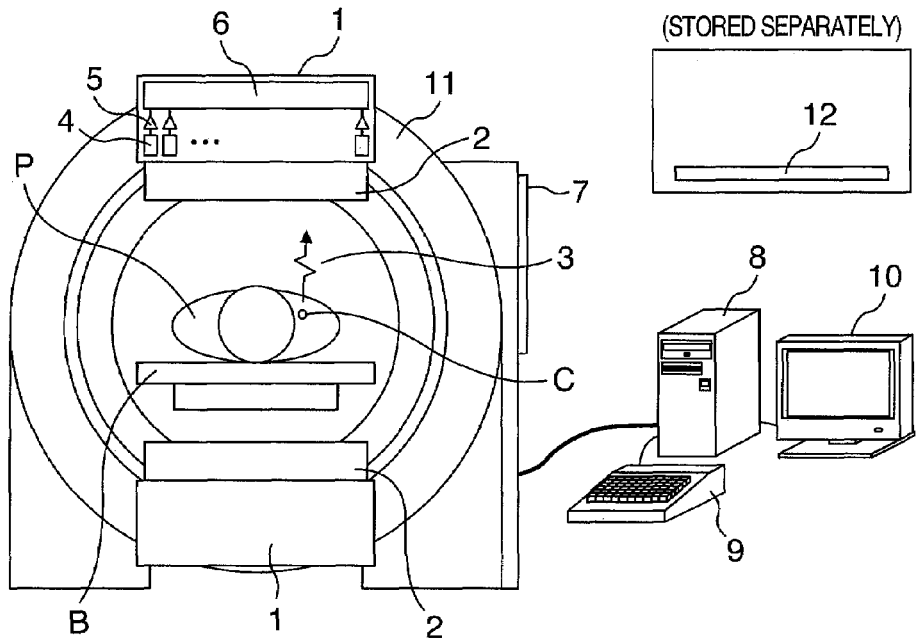
FIG. 1 is a conceptual diagram showing the configuration of a SPECT apparatus as a radiological imaging apparatus according to the present invention.

FIG. 1 shows a SPECT (Single Photon Emission Computed Tomography) apparatus.

The SPECT apparatus is equipped with a plurality of semiconductor detector units 1, a rotating support unit 11, a data collector/analyzer 8 and a display device 10. The semiconductor detector units 1 are arranged on the rotating support unit 11. Each semiconductor detector unit 1 rotates independently and it is possible to arrange two units side by side to increase an image-pickup area or use the detector unit 1 as a gamma camera for capturing plane images. Each semiconductor detector unit 1 has a plurality of semiconductor detection elements 4 and a plurality of signal amplifiers 5 and is connected to many integrated circuits of a data processing circuit 6.

A collimator 2 made of a radiation shielding member (e.g., lead, tungsten or the like) having many through holes is provided between the semiconductor detector unit 1 and an examinee P to restrict a viewing angle from the semiconductor detector units 1. Furthermore, since the semiconductor detector units 1 have a light/electromagnetic shield, influences of electromagnetic waves other than $\gamma$ rays 3 emitted from the examinee P are blocked off. The light/electromagnetic shield is formed of a material such as aluminum.

A bed B on which the examinee P to whom radiopharmaceutical has been administered is placed is equipped with a transfer mechanism and the examinee P is moved between the semiconductor detector units 1. $\gamma$ rays (annihilated $\gamma$ rays) accompanying disintegration of the radiopharmaceutical are emitted from inside the body of the examinee.

In the body of the examinee P, the $\gamma$ rays 3 emitted from an accumulation section C where radiopharmaceutical is accumulated pass through the through holes in the collimator 2 and introduced to each semiconductor detection element 4 in the semiconductor detector unit 1. Signal induced charge output from the semiconductor detection element 4 is subjected to waveform shaping and amplified by the signal amplifier 5 as a voltage signal, subjected to signal processing in the subsequent stages at the data processing circuit 6 such as an analog to digital conversion of the voltage signal peak value, an amplifier address to detector XY address conversion, acquisition of time information, real-time peak value calibration or the like.

Here, each of the semiconductor detection elements 4 has been explained as forming one pixel of an image as one detector, but a plurality of semiconductor elements may also constitute one detector.

The data collector/analyzer 8 receives data from the data processing circuit 6 and performs data saving, energy spectrum analysis, image processing or the like and the display device 10 outputs visual information to a user.

Rotation control of the rotating support unit 11, control of the distance between the semiconductor detector units 1 and examinee P and position control of the examinee P by the bed B can be performed in the neighborhood of the SPECT apparatus through an operation panel 7 or can also be performed remotely from the data collector/analyzer 8.

Next, a peak value distribution of a signal from the semiconductor detector element will be explained with reference to FIG. 2. The semiconductor detector acquires induced charge generated along with collection of electron/hole pairs due to ionization of radiation as a signal. However, when trapping of electrons and holes occurs due to an impurity level and the time until detrapping is longer than a pulse shaping time, the charge cannot contribute to the signal and results in loss of a signal peak value. In a parallel flat type semiconductor detector, assuming that:

Electron mobility: $\mu_e$ [cm/s/(V/cm)]
Hole mobility: $\mu_h$ [cm/s/(V/cm)]
Electron lifetime: $\tau_e$ [s]
Hole lifetime: $\tau_h$ [s]
Voltage: V [V]
Distance between flat plates: d [cm]
Reaction position of incident radiation: x [cm] (distance from anode)
Mean free path of electron $\lambda_e = \mu_e \cdot \tau_e \cdot V/d$ [cm]
Mean free path of hole $\lambda_h = \mu_h \cdot \tau_h \cdot V/d$ [cm] a trapping loss peak value H [% peak value without trapping] is given by:

$$H = \frac{\lambda_e}{d}\left(1 - \exp\left(-\frac{x}{\lambda_e}\right)\right) + \frac{\lambda_k}{d}\left(1 - \exp\left(-\frac{d-x}{\lambda_h}\right)\right) \quad \text{[Expression 1]}$$

Figure 2:
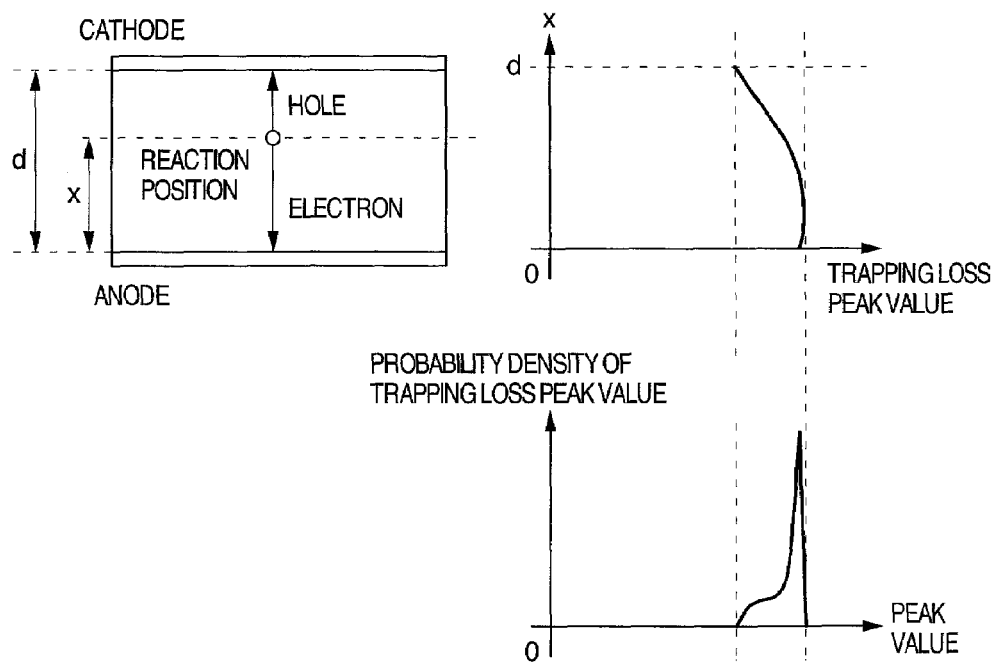
FIG. 2 shows a trapping loss peak value distribution of a semiconductor detection element.

In the case of semiconductor such as CdTe, CZT in which mean free paths differ considerably between electrons and holes, the probability density distribution of a trapping loss peak value shows notable asymmetry as shown in FIG. 2.

Of various types of radiation, γ rays used in the nuclear medicinal field have greater mean free paths with respect to an object than α rays and β rays, and therefore the reaction positions cannot be localized on the cathode side and the problem of this trapping loss is serious.

The trapping loss can be improved by simply increasing an applied voltage but there are practical limitations due to problems such as securing of insulation in a dense arrangement, increase of leakage current of semiconductor itself.

As for the radiological imaging apparatus, a large volume of the semiconductor detection element 4 per signal amplifier 5 needs to be secured from the standpoints of circuit cost and heat generation, and leakage current in particular is likely to increase and it is difficult to increase the voltage.

Furthermore, trapping loss can also be reduced using a method of adding a rise time measurement circuit and correcting a peak value based on a correlation with the rise time or a method of adding an electrode which limits an induced charge generating space called "Frisch Grid" to the vicinity of the anode, but for an application requiring a large volume measurement circuit like a radiological imaging apparatus, a cost increase becomes a problem and it is difficult to adopt such methods. As described above, when trapping loss is unavoidable, it remains an issue to be addressed how to minimize the influence thereof.

FIG. 3 shows a peak value distribution variation (mode transfer) due to the amount of superimposing noise. There are actually a plurality of noise factors other than spread of peak value distribution due to trapping loss (hereinafter, referred to as "trapping loss noise") such as noise by heat vibration of electrons and the peak value distribution obtained is a result of superimposition of those noise factors. FIG. 3 shows a superimposing noise peak value distribution when loss of 9% at maximum (x=d) or approximately 1% at minimum (signal when $(d-x)/\lambda_e = x/\lambda_h$) occurs and when the amount of other Gaussian distribution noise is changed from 1.0 to 5.0% at full width at half maximum assuming $\lambda_e/\lambda_h$ is approximately 10 which corresponds to CdTe. Even in the worst case in the figure, the energy resolution after superimposition is approximately 7.5%, which shows superiority over a conventional scintillator and is a consideration with a reasonable amount of trapping loss.

In radiation measurement, it is appreciated that a mode which is an index generally used as a representative value of a peak value distribution decreases as Gaussian distribution noise increases. When the Gaussian distribution noise increases until it becomes completely dominant, the mode drops down to a mean value of the trapping loss distribution and in the case of FIG. 3, the mode variation width is a maximum of approximately 3%.

On the other hand, the mean value of each post-superimposition distribution is invariable with respect to the amount of superimposing noise.

FIG. 4 shows nonlinearity of a mode position in an energy spectrum. Most noise such as electronic noise does not depend on input energy and an SN ratio of a signal peak value improves as the input energy increases. However, in the case of trapping loss noise, under a normal condition under which the probability of trapping of signal carriers with which trapping of signal carrier charge (electrons and holes) continues is not changed, noise is proportional to input energy and the SN ratio is not improved even with high energy measurement. Furthermore, not only the SN ratio does not improve, but also the ratio between other (Gaussian distribution) noise and trapping loss noise changes depending on the input energy, and therefore the distribution shape changes in the same way as in FIG. 3.

This indicates that even when the mode maintains linearity in a single trapping loss distribution with respect to the input energy, the mode has nonlinearity with respect to the input energy in a distribution with other noise superimposed thereon.

A plurality of signal amplifiers 5 generally have an error between gain and offset and signals obtained from the respective signal amplifiers 5 need to be calibrated. Here, "calibration" means that for a set of a plurality of radiation detection elements 4 and signal amplifiers 5, a reference value for each set on an individual spectrum is converted so as to become an identical peak value on an integrated spectrum. Therefore, a plurality of calibration coefficients are given to each set, and multiplications and additions are performed on the acquired signal values. If they are linear, full calibration is possible with two elements; gain calibration coefficient and offset calibration coefficient, but when they are nonlinear, the number of those coefficients need to be increased according to the degree, and moreover full calibration generally does not result. Hereinafter, this calibration coefficient group will be referred to as calibration data.

In an apparatus such as radiological imaging apparatus which has many signal amplifiers 5, it is not possible to use the same pulser for the respective signal amplifiers 5 for reasons related to wiring capacity noise and wiring volume cost or the like and if a pulser is created for each signal amplifier 5 individually, characteristic errors between pulsers occur and calibration data with required accuracy is not obtained. Therefore, a calibration radiation source 12 needs to be used to obtain calibration data.

Based on the above described premise, if calibration is performed using a mode on an individual spectrum as in the case of a conventional art, the above described nonlinearity becomes a problem. More specifically, when a nonlinear reference is calibrated, a calibration radiation source 12 for various kinds of energy is required and the time required to acquire calibration data (e.g., several hours/one type of energy) increases N-fold and when the calibration data increases, memory in the data processing circuit 6 is consumed and the cost required for real-time processing increases.

In contrast, trapping loss is proportional to the input energy, and for two reasons; that a mean value of the distribution is linear to the input energy and that a mean value of the actually measured peak value distribution with Gaussian distribution noise superimposed thereon matches the mean value of the trapping loss distribution, the mean value of the actually measured peak value distribution is linear to the input energy and calibration of linear energy is possible. Furthermore, since the mean value does not vary with respect to the amount of noise, calibration data need not be acquired every time a noise variation occurs (e.g., several days to several weeks) and the time interval for acquiring calibration data can be extended (e.g., one year).

Especially, when using Compton recoil electrons and photons in Compton scattering, it should be noted that securing linearity over the whole energy spectrum is important.

Furthermore, when calibration is performed with a limited count, if a mode of a distribution of an unknown shape is used, a large count needs to be taken at a position extremely close to the mode (≈required calibration accuracy, e.g., 0.1% width), the error converges slowly. If the mean value is used, the count of the whole distribution contributes to convergence of the error, and therefore high accuracy calibration in a short time is possible, which also constitutes a great advantage.

FIG. 5 is a figure showing a relationship between a noise variation and a region of interest for energy (hereinafter, referred to as an "ROI"). Assuming a leakage current variation or the like accompanying a temperature variation, a case where a Gaussian distribution noise is not constant with respect to the time will be described. The upper part of FIG. 5 shows a count leakage from the ROI with respect to a noise variation after calibration according to a mode. With a certain set A of the radiation detection element 4 and signal amplifier 5, when calibration is performed with reference to the mode when the Gaussian distribution noise is small and an ROI is set according to a certain set B having largest Gaussian distribution noise, if the Gaussian distribution noise of set A increases on a par with set B, the peak value distribution sticks out of the ROI a great deal as shown in the upper part of FIG. 5. The lower part of FIG. 5 shows a case where a mean value is used as a calibration reference. When a mean value is used as a calibration reference, unlike the upper part of FIG. 5, even when the Gaussian distribution noise of set A increases on a par with set B, it is possible to prevent the peak value distribution from considerably sticking out of the ROI. As shown above, the mean value is preferably used as an energy calibration reference for a noise variation, too.

Furthermore, as a Gaussian distribution noise which depends on the input energy, there is charge carrier generation amount statistic noise, but this is sufficiently small for the semiconductor detector while it is large as the ratio to the peak value at low energy, and it thereby tends to increase problems such as a mode variation and the above described discussions are applicable as they are, and therefore they are ignored. Likewise, trajectory loss noise, escape of characteristic X rays, escape of photoelectron and Compton recoil electrons are not main noise factors, and therefore they are ignored.

A calibration method will be explained. The calibration method detects irradiation of radiation with predetermined energy from the calibration radiation source 12 using a plurality of radiation detectors 4 having a peak value distribution whose mode is different from a mean value and performs calibration so that mean values become identical within the peak value distribution about the respective radiation detectors 4 obtained through irradiation of radiation with predetermined energy from the calibration radiation source. When the mean values within the peak value distribution of the respective radiation detectors 4 are calibrated to the same value, this calibration is performed by the data collector/analyzer 8 setting a calibration coefficient stored in the memory of the data processing circuit 6.

The calibration coefficient is calculated as follows. Data is collected using a radiation source (ST1). Average energy at each pixel is calculated (ST2). A channel is set which is an index value independently set for the energy value at each pixel. For example, a mean value is set to 1000 ch as a predetermined channel (ST3). A calibration coefficient is calculated by dividing the predetermined channel by the mean value (ST4). The output detected with the detector is calibrated using the calibration coefficient calculated in this way.

The method of setting an ROI will be explained. The ROI is set using the above described calibration method assuming the mean value within the peak value distribution through irradiation of radiation with predetermined energy as a reference of the region of interest for energy (ROI). A region in which a predetermined amount (e.g., 98%) of count is included is created from the mean value about peak value distributions of all pixels and a region about a pixel corresponding to a largest region is set as the ROI.

As described above, taking advantage that a new distribution resulting from superimposition of two distributions shares the center of gravity, a mean value of the peak value distribution is used as a calibration reference for energy of the actually measured peak value distribution which is superimposition of trapping loss noise and Gaussian distribution noise. Therefore, high energy calibration accuracy can be obtained regardless of noise and magnitude of incident energy and this has an effect equivalent to that of increasing energy resolution over the total energy region. This makes it possible to increase the rate of elimination of unnecessary signals such as scattered radiation and improve the SN ratio (image quality in the case of a radiological imaging apparatus). Since a mean value converges with respect to an acquired count more quickly than a mode, it is possible to realize collection of high accuracy calibration data in a short time. Because of the calibration technique which is not affected by a noise variation, calibration data need not be acquired every time a noise variation occurs and the time interval required to acquire calibration data can be extended. Because of linear calibration which requires only multiplications and additions, real-time energy calibration can be performed easily.

Moreover, a mean value is also used as an ROI setting reference. This eliminates omissions in a counting due to a noise variation.

This embodiment has explained the SPECT inspection apparatus so far and the present invention can also be implemented as a PET apparatus by arranging a group of detectors 180 degrees opposite to an object and adding a time detection system circuit to a peak value reading system.

The present invention is applicable not only to a semiconductor radiation detector but also to a detector using a scintillator.

A radiation detecting device is a detector unit as a group of detectors arranged 180 degrees opposite to the semiconductor detector unit 1 of the SPECT apparatus or the PET apparatus.

A radiological imaging apparatus has the radiological imaging apparatus and data collector/analyzer 8.

The semiconductor radiation detector will be explained in detail below. As a radiation detector which detects radiation such as γ rays, one using a NaI scintillator is conventionally known. In a gamma camera provided with the NaI scintillator (a kind of radiological imaging apparatus), radiation (γ rays) are introduced to the scintillator at an angle limited by many collimators, interact with NaI crystal and emit scintillation light. This light proceeds through a light guide, reaches a photomultiplier and is transformed into an electric signal. The electric signal is shaped by a measurement circuit attached to a measurement circuit fixing board and sent from an output connector to an outside data collection system. All of the scintillator, light guide, photomultiplier, measurement circuit, measurement circuit fixing board or the like are housed in a light-shielding case to shield electromagnetic waves other than outside radiation.

A gamma camera using a scintillator generally has a structure with a large photomultiplier (also called a "photomal") disposed after one large crystal such as NaI, and therefore intrinsic position resolution remains on the order of 4 mm. Furthermore, the scintillator performs detection after undergoing multi-stage conversions; from radiation to visible light and from visible light to electrons, and therefore has a problem that it has poor energy resolution. For this reason, scattered radiation which has mixed in cannot be separated and the SN ratio with respect to a signal indicating true position information on emission of γ rays deteriorates, which involves a problem of deterioration of image quality or an increase of an image capturing time. There is a PET apparatus (positron emission tomography apparatus) with position resolution on the order of 5 to 6 mm or a high-end PET apparatus with position resolution on the order of 4 mm, but they likewise include problems related to the SN ratio.

As a radiation detector which detects radiation based on a principle different from that of a scintillator, there is a semiconductor detector provided with semiconductor radiation detection elements using a semiconductor material such as CdTe (cadmium telluride), TlBr (thallium bromide), GaAs (gallium arsenide).

This semiconductor detector is attracting attention because semiconductor radiation detection elements directly convert electric charge generated through interaction between radiation and the semiconductor material to an electric signal and has therefore higher efficiency of conversion to an electric signal than that of a scintillator and has excellent energy resolution. Here, having excellent energy resolution means improvement of the SN ratio of the radiation detection signal indicating true position information, that is, improvement of detection accuracy and various effects such as improvement of contrast of an image and reduction of an image capturing time can be expected. Two-dimensional arrangement of these semiconductor radiation detection elements on a substrate allows the position of an emission source of radiation to be detected.

Compound semiconductor has a lower mobility-life product than intrinsic semiconductor and has a problem that the peak value distribution expands at an actual voltage due to a hole trapping phenomenon and the distribution becomes asymmetric. This makes impossible handling (mode=mean value or the like) as a Gaussian distribution in a conventional scintillator. Furthermore, when using a large volume of detection elements such as a radiological imaging apparatus, there may be cases where variations in the performance of each detection element occur and individual differences and time variations of noise can no longer be ignored.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An energy calibration method comprising the steps of: detecting irradiation of radiation with predetermined energy from a calibration radiation source using a plurality of radiation detectors having a peak value distribution whose mode and mean value are different; and
performing calibration so that mean values become identical within the peak value distributions of the respective radiation detectors obtained through irradiation of radiation with predetermined energy from the calibration radiation source
wherein a region of interest (ROI) is selected based on the mean value such that a count leakage from the ROI is less than with an ROI selected based on the mode value.

2. A setting method of region of interest for energy (hereinafter referred to as "ROI") using the calibration method according to claim 1, whereby a mean value in the peak value distribution through irradiation of the radiation with predetermined energy is used as a reference for the ROI.

3. The ROI setting method according to claim 2, wherein a region in which a predetermined amount of count relative to a mean value is included is created with respect to peak value distributions of all the radiation detectors and the region corresponding to the detector having a largest region is set as an ROI.

4. The energy calibration method according to claim 1, wherein when performing the calibration, a calibration coefficient is calculated by dividing an index value independently set by each detector for each energy value by the mean value and calibration is performed using the calibration coefficient.

5. The energy calibration method according to claim 1, wherein the count leakage from the ROI based on the mean value is substantially prevented.

6. The energy calibration method according to claim 1, wherein the count leakage from the ROI based on the mean values is substantially prevented.

7. A radiation detecting device comprising:
a plurality of detectors which detect radiation;
a plurality of signal amplifiers provided in correspondence with the respective detectors for amplifying outputs of the detectors; and
a data processing circuit calibrated so that mean values become identical within the peak value distributions of the respective radiation detectors obtained through irradiation of radiation with predetermined energy from the calibration radiation source which irradiates radiation
wherein a region of interest (ROI) is selected based on the mean values of respective radiation detectors such that a count leakage from the ROI is less than with an ROI selected based on corresponding mode values.

8. A radiological imaging apparatus comprising:
the radiation detecting device according to claim 7; and
a data collector/analyzer which receives data from the data processing circuit and performs the calibration on the data processing circuit.

9. The radiological imaging apparatus according to claim 8, wherein the data collector/analyzer calculates a calibration coefficient by dividing an index value independently set by each detector for each energy value by the mean value and performs calibration on the data processing circuit using the calibration coefficient.

10. The radiation detecting device according to claim 7, wherein the data processing circuit sets a region of interest for energy (hereinafter referred to as "ROI") relative to a mean value in the peak value distribution through irradiation of the radiation with predetermined energy.

11. A radiological imaging apparatus comprising:
   the radiation detecting device according to claim 10; and
   a data collector/analyzer which receives data from the data processing circuit and sets the ROI in the data processing circuit.

12. The radiological imaging apparatus according to claim 11, wherein when setting an ROI in the data processing circuit, the data collector/analyzer creates a region in which a predetermined amount of count relative to a mean value is included with respect to peak value distributions of all the radiation detectors and sets the region corresponding to the detector having a largest region as the ROI.

13. The radiation detecting device according to claim 10, wherein the data processing circuit sets a region corresponding to the detector having a largest region as an ROI out of the region created in which a predetermined amount of count relative to a mean value is included with respect to peak value distributions of all the radiation detectors.

14. The radiation detecting device according to claim 7, wherein the data processing circuit performs calibration using a calibration coefficient calculated by dividing an index value independently set by each detector for each energy value by the mean value.

* * * * *